United States Patent [19]

Townsend et al.

[11] 4,439,048
[45] Mar. 27, 1984

[54] ACCELERATING RATE CALORIMETER AND METHOD OF OPERATION

[75] Inventors: Donald I. Townsend; Richard H. Solem, both of Midland; Edward E. Timm, Coleman; Victor J. Caldecourt, Midland, all of Mich.

[73] Assignee: The Dow Chemical Co., Midland, Mich.

[21] Appl. No.: 101,937

[22] Filed: Dec. 10, 1979

Related U.S. Application Data

[60] Division of Ser. No. 906,182, May 15, 1978, Pat. No. 4,208,907, which is a continuation-in-part of Ser. No. 723,686, Sep. 16, 1976, abandoned.

[51] Int. Cl.$^3$ ............................................. G01K 17/00
[52] U.S. Cl. ..................................................... 374/34
[58] Field of Search ....................... 73/190 R; 422/51; 374/34

[56] References Cited

U.S. PATENT DOCUMENTS

| | | | |
|---|---|---|---|
| 1,247,998 | 11/1917 | Parr | 73/191 |
| 3,365,994 | 1/1968 | Hoagland | 73/190 |
| 3,765,237 | 10/1973 | Blackner | 73/190 |
| 4,088,447 | 5/1978 | Walker | 73/190 |

OTHER PUBLICATIONS

Sturtevant, "Calorimetric Investigations of Organic Reactions", in Journal of Am. Chemistry, vol. 59, 1937, pp. 1528–1537.
Hiller, Jr. et al., "Automatically Controlled Adiabatic Calorimeter", in Rev. of Sci. Inst., vol. 33 #5, 3/62, pp. 323–330.

Primary Examiner—Herbert Goldstein
Attorney, Agent, or Firm—V. Dean Clausen

[57] ABSTRACT

The accelerating rate calorimeter disclosed herein is an instrument designed for accurately determining the adiabatic thermal runaway characteristics of reactive chemicals. The mode of operation involves measuring the adiabatic self-heat rate of exothermic chemical reactions to determine the acceleration of the reaction rate as a function of temperature. The basic instrument includes a sample vessel which is positioned inside a reaction chamber. The environment surrounding the sample vessel is a gas, such as air, or an inert gas, or it can be a vacuum environment. Separate heater means are provided for heating the reaction chamber and the sample vessel.

During the exothermic reaction of the chemical in the sample vessel, the temperature of the reaction chamber and the sample vessel are continuously monitored by separate temperature sensing means. Electronic controls sense any temperature differential between the sample vessel and the reaction chamber and adjust the temperature to maintain the desired adiabatic condition for the sample vessel. The data regarding time, temperature, and self-heat rate is automatically recorded by a computer system as the reaction proceeds. This data can be used to determine the adiabatic kinetics describing the reaction. In addition, by relating the experimental time to maximum rate, as a function of temperature, the thermal runaway potential of the reactive chemical can be determined at any temperature point in the experimental range, or, by extrapolation, at any lower temperature.

1 Claim, 2 Drawing Figures

ACCELERATING RATE CALORIMETER AND METHOD OF OPERATION

CROSS REFERENCE TO RELATED APPLICATION

This is a divisional of application Ser. No. 906,182 filed May 15, 1978, now U.S. Pat. No. 4,208,907, which is a continuation-in-part of U.S. application Ser. No. 723,686 filed Sept. 16, 1976, now abandoned.

BACKGROUND OF THE INVENTION

Broadly, the invention relates to an apparatus and method for evaluating thermal hazard characteristics of reactive chemicals. More specifically, this concept is directed to a dynamic adiabatic calorimeter for measuring the self-heating rate of exothermic chemical reactions, and which is used to obtain data such as thermal runaway potential.

The term calorimetry can be generally defined as measurement of energy in the form of heat. The science of calorimetry is widely used in the chemical industry to measure the quantity of heat liberated or absorbed during chemical reactions, changes of state, formation of solutions, and the like. Heat measurement data from chemical reactions can be of value for several reasons. For example, when chemical engineers design new plants or processes, it is essential to know the heat of reaction of the chemicals involved in order to properly calculate heat balances.

Over a period of many years several different types of calorimeters have been developed for measuring heat energy. One type of calorimeter in common use is an instrument referred to as an adiabatic reaction calorimeter. In the operation of an adiabatic calorimeter, the objective is to minimize heat transfer between the vessel (bomb) which contains the reacting sample and the structure and atmosphere which surrounds the vessel. If the adiabatic condition can be successfully maintained during the chemical reaction, such a system provides an excellent means for obtaining accurate heat measurement data.

It is generally known that chemical compositions are constantly undergoing decomposition. If the decomposition reaction is exothermic, heat energy is continuously evolved until all reactants are consumed. A general rule is that the amount of heat liberated will be proportional to the rate of the reaction. In some situations, however, because of low heat conduction to the environment, the heat being liberated during reaction will accumulate in the reacting mass faster than it can be carried away. For example, this situation will frequently occur when a chemical composition begins reacting in a confined space such as a reactor or a tank car.

To explain further, when the liberated heat causes the temperature of the mass to increase, it causes the reaction to go much faster, or accelerate, as the temperature climbs. Not only does the rise in temperature cause the reaction to go faster, it actually increases the rate of reaction in an exponential manner. For example, the reaction rate for many chemical compositions will double for each 10 degree rise in temperature, at ambient temperature. At a point where the reaction mass begins to generate more heat than the system is capable of removing, the reaction will undergo a thermal runaway.

The great release of energy from a thermal runaway can oftentimes cause vaporization of the chemical. In addition, the reaction of the chemical any evolve gaseous products. These factors may result in pressuring of the vessel in which the chemical is contained, and if the strength of the vessel is inadequate, it will rupture. The resulting explosion can cause costly damage to the process or storage area and may even result in serious personal injury.

Because of the thermal runaway hazard involved in the manufacture, storage and shipping of reactive chemicals, there is need for an instrument which can predict the runaway potential, or other adverse behavior of the chemical compositions, from temperature measurement data. Several of the commercially available instruments, including some adiabatic calorimeters, are useful for determining overall reaction information, such as heat of reaction, heat of combustion, heat of formation, and the like. Some instruments, such as differential thermal analysis instruments and differential scanning calorimeters, also scan the reactive chemical relative to an inert reference sample, to determine qualitatively whether the chemical exotherms or endotherms and the relative size of the reactions. To date, however, there is no known system capable of quantitatively determining the thermal runaway characteristics of reactive chemicals.

In contrast to the prior instruments, the present invention is an accelerating rate calorimeter, which provides a unique instrument in the field of calorimetry. In this instrument we are able to simulate, on a small scale, an actual thermal runaway of a reactive chemical. Not only can a thermal runaway be simulated, but the instrument does not require a reference sample to detect the exothermic reaction. Because the data is generated in an adiabatic environment, it can be applied directly to an actual situation.

Some of the prior calorimeter instruments operate only on a temperature base, that is, they are designed to determine overall energy information by observing only the adiabatic temperature rise in exothermic reactions. By contrast, the instrument of this invention obtains data based on temperature rise as a function of time. The instrument thus generates quantitative information on the adiabatic rate of reaction in the form of self-heat rate throughout the entire temperature range of the experiment. From this data the adiabatic (non-isothermal) kinetics which describe the self-accelerating reaction can be determined.

A particularly unique feature of this instrument is the capability to relate the experimental time to maximum rate, or time of explosion, as a function of temperature. This feature enables determining the thermal runaway potential of the reactive chemical at any temperature in the range of the experiment. Also, by extrapolation, this potential can be determined for any temperature below the expermental range. This hazard information can be applied directly to establish safe conditions for manufacturing, storing and shipping of reactive chemicals.

SUMMARY OF THE INVENTION

The instrument of this invention is an accelerating rate calorimeter specifically designed to measure the adiabatic self-heat rate and the time to maximum rate of an exothermic chemical reaction, as a function of temperature. This data is useful for determining the adiabatic thermal runaway characteristics of reactive chemicals. The instrument consists of a closed sample vessel, which is positioned inside a closed reaction chamber, such that the sample vessel is surrounded by the chamber environment. The sample vessel contains a sample of the reactive chemical to be studied. A heater means is provided for the reaction chamber. A separate heater means is provided for heating the sample vessel. The vessel heater fits inside the reaction chamber and it surrounds the sample vessel.

One temperature sensor is associated with the reaction chamber, and a second temperature sensor is attached to the sample vessel. These sensors and the reaction chamber heater are associated with a temperature control unit. This control unit holds the temperature of the reaction chamber equal to the temperature of the sample vessel, to maintain the adiabatic condition for the sameple vessel. A separate temperature control unit is associated with the sample vessel heater, to regulate heat input to the sample vessel. A temperature and time recorder unit is associated with the second temperature sensor. The sample vessel is heated to a temperature at which the adiabatic self-heat rate of the reaction chemical can be detected. The reaction is then allowed to go to completion adiabatically, and the temperature of the sample vessel is continuously recorded, as a function of time.

DESCRIPTION OF A PREFERRED EMBODIMENT

Figure 1:
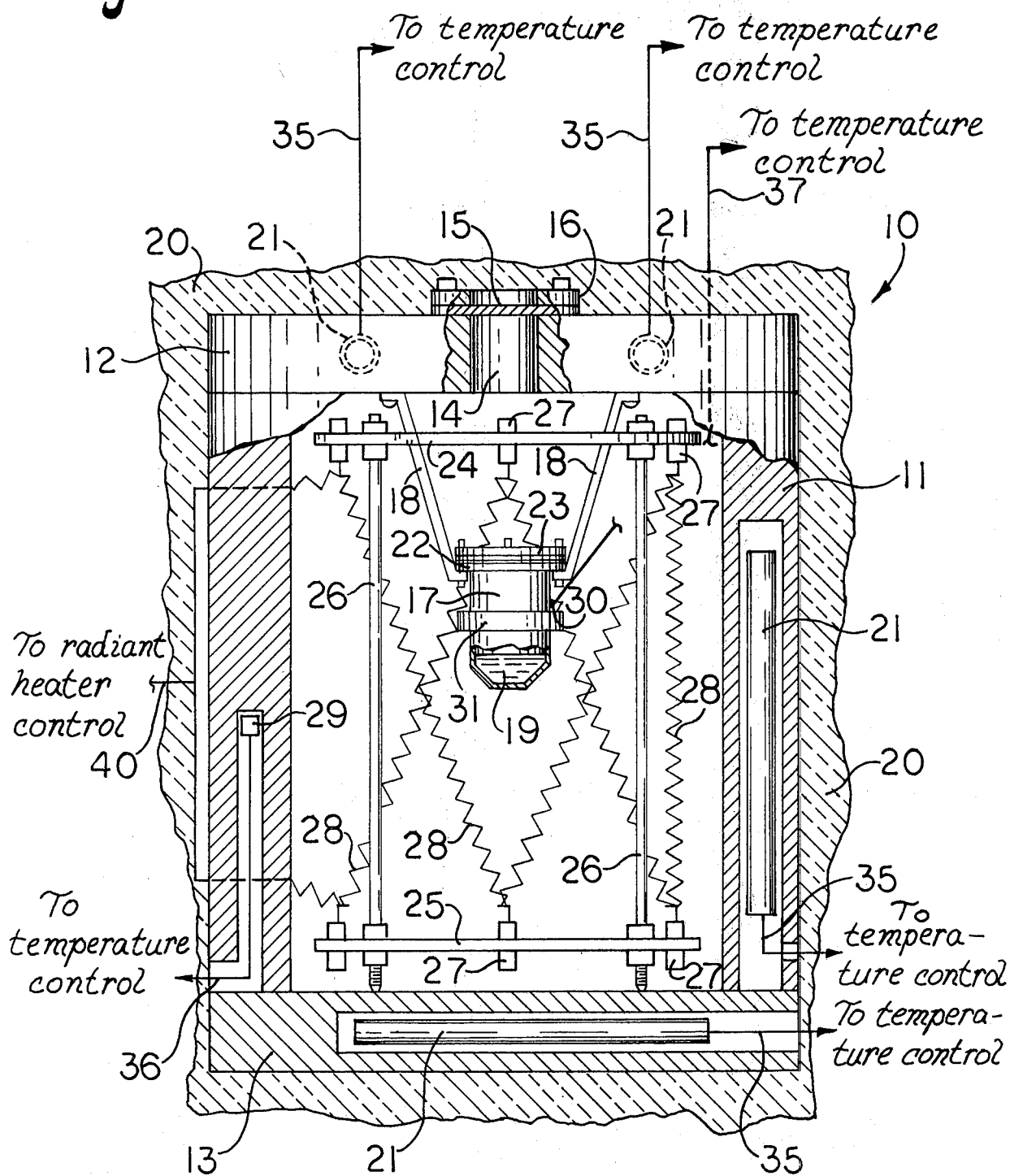
FIG. 1 is a front elevation view, mostly in section, of one embodiment of a calorimeter apparatus according to this invention.

In the drawing the apparatus illustrated in FIG. 1 is an adiabatic reaction calorimeter. The calorimeter instrument, as indicated generally by numeral 10, is defined by a closed reaction chamber, which includes the environment within the chamber. Specifically, the chamber comprises an upstanding cylindrical wall 11, a flat top wall 12, which is secured across the upper edge of wall 11, and a flat bottom wall 13, which fastens across the lower edge of wall 11. At the approximate center of top wall 12 is a vent opening 14. Opening 14 is sealed with a frangible membrane 15, which is held in place by retainer ring 16.

A closed vessel 17 is suspended inside chamber 10, the vessel being attached to the underside of top wall 12 with hanger straps 18. Vessel 17 provides a container (reaction bomb) for holding a chemical sample 19. This vessel has an open top (not shown). A flange 22 defines the outer edge of the vessel top. Fastened to flange 22 is a retainer ring 23. The opening in ring 23 (not shown) is the same size as the opening in vessel 17. The opening in vessel 17 is closed by a frangible membrane fitted between flange 22 and ring 23. Between the membrane and ring 23 is a suitable gasket.

Inside of chamber 10 the environment which surrounds vessel 17 is normally a gas phase, such as air. The gas phase can also include an inert gas, such as nitrogen. A suitable operating pressure for the gas environment is from about one (1) micron to one (1) atmosphere of absolute pressure. For some thermal studies a vacuum environment is preferred. An advantage of the vacuum environment is that it helps to reduce convective heat transfer inside of the reaction chamber 10.

It is preferred to cover the entire outer surface of chamber 10 with a layer 20 of high temperature insulation material. The insulation layer is not critical to successful operation of the calorimeter instrument. The function of the insulation layer is to reduce heat loss from chamber 10. Several cartridge heaters, each indicated by numeral 21, provide means for heating the chamber 10. Referring to the drawing, two cartridge heaters are fitted into top wall 12, and two are placed in bottom wall 13. In addition, four cartridge heaters are placed in the upstanding cylindrical wall 11. To simplify the illustration, only one cartridge heater is shown in cylindrical wall 11 and one in the bottom wall 13.

Means for heating sample vessel 17 is provided by a radiant heater unit. The structure of the radiant heater includes an upper ring 24, a lower ring 25, and support rods 26, which hold the rings together. The heater structure actually has four support rods 26, but only two are shown in the drawing. In ring 24 and ring 25 there are four insulators, each indicated by numeral 27. In the drawing only three insulators 27 are shown in each ring. Several single strand wire heater elements, each indicated by numeral 28, are stretched between the rings 24 and 25. The ends of each heater element are anchored to an insulator 27. As shown in the drawing, when the radiant heater unit is in operating position, it sets inside the reaction chamber 10 and it completely surrounds the sample vessel 17.

Figure 2:
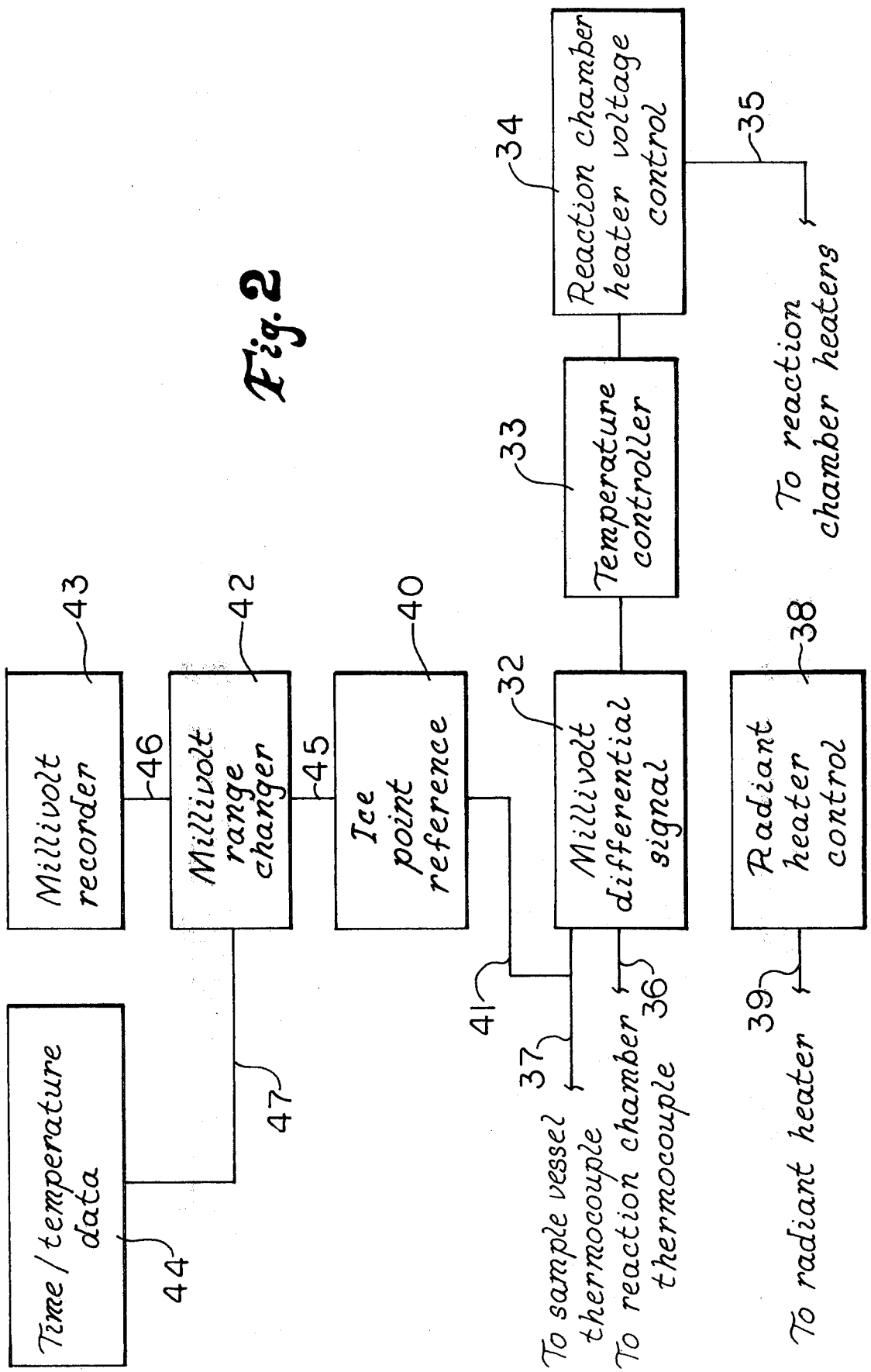
FIG. 2 is a schematic drawing illustrating an electronic temperature control and recording system which forms a part of the apparatus shown in FIG. 1.

The temperature of reaction chamber 10 is monitored by a single thermocouple 29, which fits into the cylindrical upstanding wall 11. The temperature of sample vessel 17 is monitored by a thermocouple 30, which is secured to the outer surface of the sample vessel by a metal strip 31. An electronic temperature control unit provides means for controlling the temperature of chamber 10, such that the temperature of the reaction chamber is equal to the temperature of the sample vessel 17. This control thus insures the required adiabatic condition for the sample vessel 17. As shown in FIG. 2, this control unit includes three components. Specifically, these components include a millivolt differential signal 32, a temperature controller 33, and a heater voltage control 34.

Thermocouple 29 connects into signal 32 through electrical lead 36, and lead 37 connects the thermocouple 30 into signal 32. The entire temperature control unit is connected into a common power supply (not shown). The cartridge heaters 21 are connected into the heater control 34 by an electrical lead 35. The power to the radiant heater unit is controlled automatically or manually through heater control 38. An electrical lead 39 connects the radiant heater into control 38. In turn, the heater control 38 is connected into a power supply (not shown). A constant temperature reference for the output of thermocouple 30 on sample vessel 17 is provided by an ice point reference 40. This reference provides a cold junction, which is electrically compensated for 0° C., the ice point of water. A lead 41 connects thermocouple 30 into the ice point reference.

During the reaction of the sample 19 in vessel 17, the temperature sensed by thermocouple 30 is continuously recorded, as a function of time, by a temperature and time recorder unit. Basic components of this unit include a millivolt range changer 42, a millivolt strip chart recorder 43, and a computer program 44. The computer program 44 issues a printout of the time-temperature data and the corresponding self-heat rate values. As shown in FIG. 2, the range changer 42 connects directly into reference thermocouple 40 through an electrical lead 45. In turn, the range changer 42 connects into recorder 43 through a lead 46, and a lead 47 connects the range changer into the computer 44.

Generally, in a typical experiment, the reactive chemical sample is loaded into the sample vessel 17 and the vessel is placed inside the reaction chamber 10. Following this step the reaction chamber, the environment within the chamber, and the sample vessel are heated up to a temperature at which the adiabatic self-heat rate of the chemical sample can be detected. At this point the exotherm has commenced and the reaction is allowed to proceed to completion in an adiabatic environment. As the reaction proceeds the temperature of the sample vessel is continuously monitored and recorded, as a function of time, and the self-heating rate of the reaction is simultaneously determined from the time-temperature data.

A typical thermal runaway study on a chemical composition which undergoes an exothermic reaction will now be described to illustrate the practice of this invention. The sample used in this study is a known organic liquid composition, namely, di-t-butyl peroxide, which has the formula $(CH_3)_3-C-O-O-C-(CH_3)_3$. When the sample composition 19 is placed in vessel 17 it will occupy about 80 percent, by volume, of the vessel. The extra space is provided to allow for generation of gas during the exotherm.

Once the sample vessel is in place in the reaction chamber 10, power is applied to the radiant heater to increase the temperature of this vessel. The temperature is brought up gradually, for example, in increments of about (5° C.). Following each increase the temperature of the reaction chamber and the sample vessel is allowed to come to equilibrium. At each equilibrium point the adiabatic self-heat rate of the sample is measured. At low temperatures, the self-heat rate is very small and thus below the detection capability of the instrument. The step-wise heating procedure is repeated until a significant self-heat rate can be observed, typically about 0.01° C. per minute.

An alternative procedure to the step-wise heat and search technique, as described above, may be used to detect the point at which the exothermic reaction commences. For example, at the start of the experiment the radiant heater can be turned on to achieve a low heat ramp of the sample vessel temperature. At low temperatures, where the rate of reaction of the chemical is very low, the ramp will be nearly constant. At higher temperatures, however, the rate of reaction and, therefore, heat generation, will be significantly higher, so that it causes the overall ramp to increase considerably. At the point where this deviation is detected, the radiant heater is turned off and the system is allowed to proceed adiabatically.

When the exothermic reaction is detected by the instrument, the computer program 44 will simultaneously record three types of data on the printout. One type of data is the temperature of the reaction, which is measured at fixed temperature increments, such as 1° C. A second type of data is the experimental run time. The time data is actually the elapsed time required for the reaction to reach each of the temperature points which are measured and recorded. The third type of data is the adiabatic self-heat rate of the reaction. This self-heat rate value is the ratio of the temperature increment divided by the time interval. A fourth type of data is the time to maximum rate, which is determined from the time-temperature data after the experiment is complete. This type of data is explained more fully below.

Following initial detection of the exotherm, the adiabatic self-heat rate will accelerate, that is, it will go faster as the temperature increases. This occurrence is characteristic of a thermal runaway. From the data printout of the computer, the technician can readily observe the point in the reaction at which the maximum rate of decomposition of the chemical substance occurs. The point of maximum decomposition rate will be that point at which the self-heat rate of the reaction is highest. The total amount of time required for the reaction to go from any given temperature during reaction, to the point of maximum reaction rate, is defined as the time to maximum rate, or time to explosion. After the maximum rate point, the reaction rate will slow down, thus causing the self-heat rate to decrease. The reason that the reaction rate slows down beyond the point of maximum decomposition rate, is because the quantity of material available for the reaction becomes correspondingly less as the reaction proceeds.

As explained earlier, the basic function of this instrument is to provide adiabatic time to maximum rate data for thermal hazard prediction. In addition, by using mathematical procedures which have been specially developed, the time-temperature and self-heat rate experimental data can be extended to provide other thermodynamic and kinetic data. For example, in a single study it is possible to generate information such as time to maximum rate, adiabatic temperature rise, heat of reaction, rate of reaction (vs. temperature), number of reactions, order of each reaction, heat of reaction (each reaction), activation energy (each reaction), and prediction of the temperature of no return for non-adiabatic systems.

In the practice of this invention, as explained above, the temperature at which maximum rate of decomposition of a chemical sample takes place is considered as the temperature at which an explosion can occur. However, as a practical matter, explosion does not always occur at the point of maximum rate of decomposition. For example, the chemical may begin to polymerize, or to assume some other condition which represents a change of state. However, if the chemical sample should explode during reaction in the sample vessel, it is assumed that the substance is at the point of maximum rate of decomposition at the time of explosion.

The data obtained in the thermal runaway study of the peroxide compound described above is set out in the following table:

TABLE

Thermal Runaway Data for Di-t-Butyl Peroxide

| Temperature of the Reaction (in °C.) | Elapsed Time into the Run (in seconds) | Self-Heat Rate of the Reaction (in. °C. per minute) | Time to Maximum Rate (in seconds) |
|---|---|---|---|
| (a)96.6 | 3,212 | 0.0062 | 101,775 |
| 98.0 | 21,197 | 0.0054 | 83,790 |
| 100.1 | 39,183 | 0.0080 | 65,804 |
| 102.9 | 57,168 | 0.0113 | 47,819 |
| 107.8 | 77,430 | 0.0185 | 27,557 |
| 116.7 | 93,669 | 0.0506 | 11,318 |
| 121.8 | 98,019 | 0.0868 | 6,968 |
| 129.0 | 101,465 | 0.1794 | 3,522 |
| 135.0 | 102,973 | 0.3021 | 2,014 |
| 143.4 | 104,038 | 0.6952 | 949 |
| 148.5 | 104,396 | 1.020 | 541 |
| 156.0 | 104,697 | 1.970 | 290 |
| 161.4 | 104,818 | 3.170 | 169 |
| 170.1 | 104,927 | 5.940 | 60 |

TABLE-continued
Thermal Runaway Data for Di-t-Butyl Peroxide

| Temperature of the Reaction (in °C.) | Elapsed Time into the Run (in seconds) | Self-Heat Rate of the Reaction (in. °C. per minute) | Time to Maximum Rate (in seconds) |
|---|---|---|---|
| [b]178.5 | 104,487 | 9.600 | 0 |
| 186.4 | 105,100 | 1.100 | — |
| 189.4 | 110,389 | 0.0229 | — |
| 192.1 | 130,219 | 0.0049 | — |

[a]Initial detection of the exothermic reaction.
[b]The point of maximum reaction rate of the reactive chemical.

From the data in the table, the following observations can be made. First, when the temperature of the chemical composition in sample vessel 17 had reached 96.6° C., the self-heat rate of the exothermic reaction could be detected. The time period of 3,212 seconds is the time required for the calorimeter system to heat the composition from ambient temperature to the point where the exotherm was detected. In other words, beyond this temperature, the self-heat being generated by the system will allow the reaction to go to completion adiabatically without adding additional heat to the sample vessel. Secondly, it will be noted that when the temperature of the reaction had reached 178.5° C., the self-heat rate of the reaction had reached a maximum of 9.60° C. per minute. The total time required for the reaction to proceed from the initial detection of the exotherm (at 96.6° C.) to the maximum rate point is the difference between the two time values, which is 101,755 seconds. The time to maximum rate from any of the temperature points during the reaction can be calculated in a similar manner. This means that the thermal runaway potential of the chemical under study is known at any given temperature throughout the entire experimental range. Further, by extrapolation, the time to maximum rate at any lower temperature can be predicted. If the thermal inertia observed in the experiment, which is the load ratio of sample to sample vessel, corresponds to the ratio values of an actual situation, such information can be applied directly to establish life conditions for manufacturing, storing and shipping of the reactive chemical. Suitable correction of the data can be performed to apply the results to other loading values.

At this point, details regarding materials of construction, general operating conditions, and other embodiments, will be discussed. These details are for the purpose of further explaining this concept, but are not intended as a limitation on the practice of the invention.

Reaction chamber 10 is constructed of nickel-plated copper; the nickel plate is applied by an electroless process. In general, the sample vessel 17 can be constructed of any material which will withstand the temperature, the pressure, and the environment conditions involved, and which is compatible with the chemical sample being tested. An an example, if the chemical composition being studied is usually stored or shipped in an aluminum vessel, it is desirable to fabricate the sample vessel of aluminum. The objective is to provide the necessary compatibility and to achieve a more accurate prediction of the actual behavior of the composition during storage or shipping.

Referring to the cartridge heaters 21, the size of each heater cartridge is determined by actual heat capacity of the metal walls which make up the reaction chamber 10. The objective is to provide uniform heat at all points in the reaction chamber. Other suitable heater means for chamber 10 would include electrical tape, heating pads, and the like. Thermocouple 29 in chamber 10 is electrically insulated from the sample vessel with a composition consisting of sodium silicate and glass braid. Any commercially available thermocouple is suitable for use with the particular metal structures of chamber 10 and sample vessel 17. In situations where a more precise heat control for chamber 10 is desired, more than one thermocouple can be used in the reaction chamber. For example, a zone temperature control can be achieved by placing thermocouples in each wall of the reaction chamber, with each zone being controlled independently by a separate temperature control unit.

When the chemical sample in the sample vessel 17 is reacting slowly, and therefore has a low self-heat rate, the temperature of the chemical and the sample are nearly equal. This constant temperature is the result of uniform conduction of the heat throughout the sample and the vessel. However, at very high self-heat rates the heat transfer between the reacting chemical and the sample vessel becomes inadequate. In other words, heat from the reaction is generated faster than it can be conducted uniformily throughout the chemical sample and the vessel. This situation causes the reacting chemical to thermally run away from the sample vessel. Because the thermocouple 30 measures the temperature of the reacting system on the outer surface of the sample vessel 17, the temperature data observed at very high self-heat rates does not reflect the true condition of the reacting chemical. This problem can be overcome by positioning a separate small diameter thermocouple inside the sample vessel, so that it is in direct contact with the test sample. Use of an appropriate fitting enables the sample vessel to be sealed at all times during the reaction. In this embodiment the thermocouple in the sample vessel is connected directly into the reference temperature thermocouple 40, and the reading from the sample is continuously monitored and compared with the outside surface temperature of the sample vessel during the thermal runaway. This embodiment is not shown in the drawing.

The radiant heater for sample vessel 17, the upper ring 24, lower ring 25, and support rods 26 are constructed of stainless steel. The heater elements 28 are conventional nichrome wire elements and the insulators 27 are an alumina composition. The insulation layer 20 is a high temperature, alumina-silica ceramic fiber. The frangible membrane 15, which closes vent opening 14, is a thin, nickel sheet metal. A similar frangible membrane, which fits across the opening in sample vessel 17, is also a nickel metal. Generally speaking, any light weight material which is compatible with the calorimeter system and which has the necessary strength may be used for the frangible membranes.

The frangible membranes provide a safety feature in the operation of this calorimeter instrument. For example, if the gas pressure created by the reaction taking place in sample vessel 17 exceeds a certain limit, it will rupture the frangible membrane on the sample vessel. When this occurs, the sudden pressure release in the chamber 10 may also be high enough to rupture the frangible membrane 15. In either situation, the frangible membrane acts as a safety valve which prevents destruction of the sample vessel and other components of the calorimeter system.

Broadly, the calorimeter instrument of this invention is useful for conducting thermal hazard studies on reactive chemical compositions. Specifically, studies can be run on organic or inorganic compounds in the form of solids, liquids, or gases, which exist either as mixtures or pure materials. The normal operating temperature range of the instrument is from about −20° C. to 500° C. The instrument also has the capability for measuring the adiabatic self-heat rate of a chemical reaction over a range of from about 0.001° C. per minute to 1000° C. per minute. Typically, this temperature range will be from about 0.010° C. per minute to 100° C. per minute.

In addition to measuring heat energy generated in a reaction, the present calorimeter instrument can be utilized to measure the pressure developed during the reaction. This can be done by attaching a pressure transducer to the sample vessel 17. The transducer is, in turn, connected into a millivolt recorder, such as the recorder 43. In response to the pressure developed in vessel 17, the transducer sends a signal to the recorder, which gives a readout in pressure units. To simplify the description, this embodiment is not illustrated in the drawing.

Although endothermic reactions are not hazardous from the standpoint of thermal runaway, gas evolution in such reactions can rupture the vessel in which the chemical is contained. The capability of this instrument to scan the pressure inside the sample vessel, as a function of temperature, enables determining the point at which substantial gas evolution occurs. Such information is useful or designing systems for safe handling of reactive chemicals.

For some chemical studies, it may be desirable to agitate the sample 19. For example, one purpose in doing this would be to obtain a homogeneous composition. The agitation step could be done by any of several techniques, such as placing the entire instrument in a mechanical shaker device, or by shaking the hanger straps 18, which hold the sample vessel in place within the reaction chamber. Another technique would be to use a magnetically driven stirring bar in the sample vessel. These embodiments are not illustrated in the drawing.

The invention claimed is:

1. A method for measuring the adiabatic self-heat rate, and the time to maximum rate of an exothermic chemical reaction, as a function of temperature, to determine the adiabatic thermal runaway characteristics of reactive chemicals, the method comprising the steps of:

placing a sample of a reactive chemcal (19) in a sample vessel (17) and closing said vessel;

positioning the closed sample vessel (17) inside of a reaction chamber (10), such that said vessel is surrounded by the environment of the chamber;

heating the sample vessel (17) in fixed temperature increments to a temperature at which the adiabatic self-heat rate of the exothermic reaction is detectable by a time and temperature recorder unit (42, 43, 44);

allowing the reaction to go to completion adiabatically and recording the adiabatic self-heat rate of the reactive chemical, by using a time and temperature recorder unit (42, 43, 44) during the course of the reaction;

holding the temperature of the reaction chamber (10) and the environment in said chamber, at the same temperature as the sample vessel (17), to maintain an adiabatic condition for the sample vessel (17); and continuously sensing the temperature of the sample vessel (17) during the reaction; and continuously recording the temperature of the sample vessel (17) as a function of time, in the time and temperature recorder unit (42, 43, 44), to thereby derive the time to maximum rate for said reaction.

* * * * *

UNITED STATES PATENT AND TRADEMARK OFFICE
CERTIFICATE OF CORRECTION

PATENT NO. : 4,439,048

DATED : March 27, 1984

INVENTOR(S) : Donald I. Townsend, et al.

It is certified that error appears in the above—identified patent and that said Letters Patent is hereby corrected as shown below:

Col. 2, line 1, delete "any" and insert --may--.
Col. 3, line 14, delete "sameple" and insert --sample--.
Col. 3, line 19, delete "reaction" and insert --reactive--.
Col. 7, line 43, delete "life" and insert --safe--.
Col. 7, line 58, delete "An", first occurrence, and insert --As--.
Col. 9, line 29, delete "or" and insert --for--.
Col. 10, Claim 1, line 11, delete "chemcal" and insert --chemical--.

Signed and Sealed this

Thirtieth Day of October 1984

[SEAL]

Attest:

Attesting Officer

GERALD J. MOSSINGHOFF

Commissioner of Patents and Trademarks